United States Patent [19]

Wu et al.

[11] Patent Number: 6,114,515
[45] Date of Patent: Sep. 5, 2000

[54] PIGRL-1, A MEMBER OF IMMUNOGLOBULIN GENE SUPERFAMILY

[75] Inventors: Shujian Wu, Levittown; Raymond W. Sweet, Bala Cynwyd; Alemseged Truneh, West Chester, all of Pa.

[73] Assignee: SmithKline Beecham Corporation, Philadelphia, Pa.

[21] Appl. No.: 08/961,564

[22] Filed: Oct. 30, 1997

Related U.S. Application Data

[60] Provisional application No. 60/056,935, Aug. 25, 1997.

[51] Int. Cl.$^7$ .......................... C07H 21/02; C07H 21/04; C12N 5/10; C12N 15/12
[52] U.S. Cl. ..................... 536/23.5; 536/23.1; 536/23.2; 536/23.53; 536/23.51; 536/23.4; 435/320.1; 435/325; 435/252.3; 435/243
[58] Field of Search ................................. 536/23.1, 23.2, 536/23.5, 23.53, 23.51, 23.4; 435/320.1, 325, 252.3, 243

[56] References Cited

PUBLICATIONS

Ngo et al. "Chapter 14" from "The Protein Folding Problem and Tertiary Structure Predictions" Ed. Merz, Jr. et al., Birkhauser, 1994, pp. 491–495.

Hillier et al., Genebank Accession WO1276, NID g1273256, EST Apr. 18, 1996.

GenBank Accession #U06431, May 26, 1995.

GenBank Accession #AA509857, Jul. 8, 1997.

Piskurich, J.F. et al., "Molecular Cloning of the Mouse Polymeric Ig Receptor", J. Immunol. 154:1735–1747 (1995).

Krajci, P. et al., "Molecular cloning and exon–intron mapping of the gene encoding human transmembrane secretory component (the poly–Ig receptor)", Eur. J. Immunol., 22:2309–2315 (1992).

*Primary Examiner*—Ronald B. Schwadron
*Attorney, Agent, or Firm*—William T. Han; Ratner & Prestia; William T. King

[57] ABSTRACT

PIGRL-1 polypeptide and polynucleotides and methods for producing such polypeptides by recombinant techniques are disclosed. Also disclosed are methods for utilizing PIGRL-1 polypeptide and polynucleotides in the design of protocols for the treatment of Hyper-IgM Immunodeficiency (HIM), X-linked Severe Combined Immunodeficiency (XSCID), and IgA deficiency (IgA-D), among others and diagnostic assays for such conditions.

7 Claims, No Drawings

PIGRL-1, A MEMBER OF IMMUNOGLOBULIN GENE SUPERFAMILY

This application claims the benefit of U.S. Provisional Application No. 60/056,935, filed Aug. 25, 1997.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Immunoglobulin superfamily, hereinafter referred to as PIGRL-1. The invention also relates to inhibiting or activating the action of such polynucleotides and polypeptides.

BACKGROUND OF THE INVENTION

The immunoglobulin (Ig) gene superfamily comprises a large number of cell surface glycoproteins that share sequence homology with the V and C domains of antibody heavy and light chains. These molecules function as receptors for antigens, immunoglobulins and cytokines as well as adhesion molecules, and play important roles in regulating the complex cell interactions that occur within the immune system (A. F. Williams et al., Annu. Rev. Immuno. 6:381–405, 1988, T. Hunkapiller et al., Adv. Immunol. 44:1–63, 1989).

Several human immunodeficiency diseases derive from gene defects or from functional deregulation of the Ig superfamily proteins. Examples are Hyper-IgM Immunodeficiency (HIM) caused by a defect in the gene encoding the ligand for CD40 (R. C. Allen et al., Science 259:990–993, 1993), X-linked Severe Combined Immunodeficiency (XSCID) caused by mutations of the IL-2 receptor (M. Noguchi et al., Cell 73:147–157, 1993) and IgA deficiency (IgA-D) linked to HLA-DQb (M. A. French et al., Immunol. Today 11:271–274, 1990).

This indicates that these receptors have an established, proven history as therapeutic targets. Clearly there is a need for identification and characterization of rather receptors which can play a role in preventing, ameliorating or correcting dysfunctions or diseases, including, but not limited to, Hyper-IgM Immunodeficiency (HIM), X-linked Severe Combined Immunodeficiency (XSCID), and IgA deficiency (IgA-D).

SUMMARY OF THE INVENTION

In one aspect, the invention relates to PIGRL-1 polypeptides and recombinant materials and methods for their production. Another aspect of the invention relates to methods for using such PIGRL-1 polypeptides and polynucleotides. Such uses include the treatment of Hyper-IgM Immunodeficiency (HIM), X-linked Severe Combined Immunodeficiency (XSCID), and IgA deficiency (IgA-D), among others. In still another aspect, the invention relates to methods to identify agonists and antagonists using the materials provided by the invention, and treating conditions associated with PIGRL-1 imbalance with the identified compounds. Yet another aspect of the invention relates to diagnostic assays for detecting diseases associated with inappropriate PIGRL-1 activity or levels.

DESCRIPTION OF THE INVENTION

Definitions

The following definitions are provided to facilitate understanding of certain terms used frequently herein.

"PIGRL-1" refers, among others, to a polypeptide comprising the amino acid sequence set forth in SEQ ID NO:2, or an allelic variant thereof.

"Receptor Activity" or "Biological Activity of the Receptor" refers to the metabolic or physiologic function of said PIGRL-1 including similar activities or improved activities or these activities with decreased undesirable side-effects. Also included are antigenic and immunogenic activities of said PIGRL-1.

"PIGRL-1 gene" refers to a polynucleotide comprising the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J Molec Biol* (1990) 215:403).

As an illustration, by a polynucleotide having a nucleotide sequence having at least, for example, 95% "identity" to a reference nucleotide sequence of SEQ ID NO: 1 is intended that the nucleotide sequence of the polynucleotide is identical to the reference sequence except that the polynucleotide sequence may include up to five point mutations per each 100 nucleotides of the reference nucleotide sequence of SEQ ID NO: 1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO: 2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

Polypeptides of the Invention

In one aspect, the present invention relates to PIGRL-1 polypeptides (or PIGRL-1 proteins). The PIGRL-1 polypeptides include the polypeptides of SEQ ID NOS:2 and 4; as well as polypeptides comprising the amino acid sequence of SEQ ID NO:2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within PIGRL-1 polypeptides are polypeptides having the amino acid sequence which have at least 80% identity to the polypeptide having the amino acid sequence of SEQ ID NO: 2 over its entire length, and still more preferably at least 90% identity, and even still more preferably at least 95% identity to SEQ ID NO: 2. Furthermore, those with at least 97–99% are highly preferred. Preferably PIGRL-1 polypeptides exhibit at least one biological activity of the receptor.

The PIGRL-1 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the PIGRL-1 polypeptides are also included in the invention. A fragment is a polypeptide having an amino acid sequence that entirely is the same as part, but not all, of the amino acid sequence of the aforementioned PIGRL-1 polypeptides. As with PIGRL-1 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of PIGRL-1 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of PIGRL-1 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate receptor activity, including those with a similar activity or an improved activity, or with a decreased undesirable activity. Also included are those that are antigenic or immunogenic in an animal, especially in a human.

Preferably, all of these polypeptide fragments retain the biological activity of the receptor, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted added in any combination.

The PIGRL-1 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to PIGRL-1 polynucleotides. PIGRL-1 polynucleotides include isolated polynucleotides which encode the PIGRL-1 polypeptides and fragments, and polynucleotides closely related thereto. More specifically, PIGRL-1 polynucleotide of the invention include a polynucleotide comprising the nucleotide sequence contained in SEQ ID NO:1 encoding a PIGRL-1 polypeptide of SEQ ID NO: 2, and polynucleotides having the particular sequences of SEQ ID NOS:1 and 3. PIGRL-1 polynucleotides further include a polynucleotide comprising a nucleotide sequence that has at least 80% identity over its entire length to a nucleotide sequence encoding the PIGRL-1 polypeptide of SEQ ID NO:2, and a polynucleotide comprising a nucleotide sequence that is at least 80% identical to that of SEQ ID NO: 1 over its entire length. In this regard, polynucleotides at least 90% identical are particularly preferred, and those with at least 95% are especially preferred. Furthermore, those with at least 97% are highly preferred and those with at least 98–99% are most highly preferred, with at least 99% being the most preferred. Also included under PIGRL-1 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such PIGRL-1 polynucleotides.

PIGRL-1 of the invention is structurally related to other proteins of the Immunoglobulin superfamily, as shown by the results of sequencing the cDNA encoding human PIGRL-1. The cDNA sequence of SEQ ID NO:1 contains an open reading frame (nucleotide number 146 to 1315) encoding a polypeptide of 390 amino acids of SEQ ID NO:2. The amino acid sequence of Table 1 (SEQ ID NO:2) has about 41.51% identity (using BLASTX) in 53 amino acid residues with Mouse polymeric immunoglobulin receptor (J. F. Piskurich et al., J. Immunol. 150:1735–1747, 1995). Furthermore, PIGRL-1 is 38.18% identical to human polymeric immunoglobulin receptor over 55 amino acid residues (P. Krajci et al., Eur. J. Irmunol. 22:2309–2315, 1992). The nucleotide sequence of Table 1 (SEQ ID NO:1) has about 66.25% identity (using BLASTN) in 80 nucleotide residues with Rana catesbeiana myosin II (C. F. Solc et al., Aud. Neurosci. 1:63–75, 1994). Thus, PIGRL-1 polypeptides and polynucleotides of the present invention are expected to have, inter alia, similar biological functions/properties to their homologous polypeptides and polynucleotides, and their utility is obvious to anyone skilled in the art.

TABLE 1[a]

```
   1 ACGAGCCTCA TCGTCAAGCT TTGTTCCTCG TGGGGGCTAG AAATCTCTTT
  51 CCAGTTCCAG ATTGTGAAGG GTTCCTGAGT AAGCAGCGTG TCTCCATCCC
 101 CCTCTCTAGG GGCTCTTGGA TGGACCTTGC ACTCTAGAAG GGACAATGGA
 151 CTTCTGGCTT TGGCCACTTT ACTTCCTGCC AGTATCAGGG GCCCTGAGGA
 201 TCCTCCCAGA AGTAAAGGTA GAGGGGGAGC TGGGCGGATC AGTTACCATC
 251 AAGTGCCCAC TTCCTGAAAT GCATGTGAGG ATATATCTGT GCCGGGAGAT
 301 GGCTGGATCT GGAACATGTG GTACCGTGGT ATCCACCACC AACTTCATCA
 351 AGGCAGAATA CAAGGGCCGA GTTACTCTGA AGCAATACCC ACGCAAGAAT
 401 CTGTTCCTAG TGGAGGTAAC ACAGCTGACA GAAAGTGACA GCGGAGTCTA
 451 TGCCTGCGGA GdGGGCATGA ACACAGACCG GGGAAAGACC CAGAAAGTCA
 501 CCCTGAATGT CCACAGTGAA TACGAGCCAT CATGGGAAGA GCAGCCAATG
 551 CCTGAGACTC AAAATGGTT TCATCTGCCC TATTTGTTCC AGATGCCTGC
 601 ATATGCCAGT TCTTCCAAAT TCGTAACCAG AGTTACCACA CCAGCTCAAA
 651 GGGGCAAGGT CCCTCCAGTT CACCACTCCT CCCCCACCAC CCAAATCACC
 701 CACCGCCCTC GAGTGTCCAG AGCATCTTCA GTAGCAGGTG ACAAGCCCCG
 751 AACCTTCCTG CCATCCACTA CAGCCTCAAA AATCTCAGCT CTGGAGGGGC
 801 TGCTCAAGCC CCAGACGCCC AGCTACAACC ACCACACCAG GCTGCACAGG
 851 CAGAGAGCAC TGGACTATGG CTCACAGTCT GGGAGGGAAG GCCAAGGATT
 901 TCACATCCTG ATCCCGACCA TCCTGGGCCT TTTCCTGCTG GCACTTCTGG
 951 GGCTGGTGGT GAAAAGGGCC GTTGAAAGGA GGAAAGCCCT CTCCAGGCGG
1001 GCCCGCCGAC TGGCCGTGAG GATGCGCGCC CTGGAGAGCT CCCAGAGGCC
1051 CCGCGGGTCG CCGCGACCGC GCTCCCAAAA CAACATCTAC AGCGCCTGCC
1101 CGCGGCGCGC TCGTGGAGCG GACGCTGCAG GCACAGGGGA GGCCCCCGTT
1151 CCCGGCCCCG GAGCGCCGTT GCCCCCCGCC CCGCTGCAGG TGTCTGAATC
1201 TCCCTGGCTC CATGCCCCAT CTCTGAAGAC CAGCTGTGAA TACGTGAGCC
1251 TCTACCACCA GCCTGCCGCC ATGATGGAGG ACAGTGATTC AGATGACTAC
1301 ATCAATGTTC CTGCCTGACA ACTCCCCAGC TATCCCCCAA CCCCAGGCTC
1351 GGACTGTGGT GCCAAGGAGT CTCATCTATC TGCTGATGTC CAATACCTGC
1401 TTCATGTGTT CTCAGAGCCC TCATCACTTC CCATGCCCCA TCTCGACTCC
1451 CATCCCCATC TATCTGTGCC CTGAGCATGG CTCTGCCCCC AGGTCGTCTT
1501 GCACACCTTG GCAGCCCCT GTAGTTGACA GGTAAGCTGT AGGCATGTAG
1551 AGCAATTGTC CCAATGCCAC TTGCTTCCTT TCCAAGCCGT CGAACAGACT
1601 GTGGGATTTG CAGAGTGTTT CTTCCATGTC TTTGACCACA GGGTTGTTGC
1651 TGCCCAGGCT CTAGATCACA TGGCATCAGG CTGGGGCAGA GGCATAGCTA
1701 TTGTCTCGGG CATCCCTTCC CAGGGTTGGG TCTTACACAA ATAGAAGGCT
1751 CTTGCTCTGA GTTATGTGAC ATGCCTCAGC CCCATGGACT AAGCAGGGGT
1801 CTGGTATAAA AACACTCCTG GAAACGCCTT TGCCCTGATC CAAATGTTAG
1851 CACTTGCTAG TGAACGTCTA CTTATCTCAA GTTCTATGCT AAAGGCAATT
```

TABLE 1ᵃ-continued

```
1901 TATCTTGATG TGATGATAAA CCAAACTTAT TAGCAAGATA TGCATATATA

1951 TCCATAAATT CTCTTTACTC TGTCTCCATC ACTTGATGCA CATAAGTGCC

2001 CTGACCTCAG CATCTCCCCT CTAAAAAAAA AAAAAAAAAA
```

ᵃA nucleotide sequence of a human PIGRL-1 (SEQ ID NO: 1).

TABLE 2ᵇ

```
  1 MDFWLWPLYF LPVSGALRIL PEVKVEGELG GSVTIKCPLP EMVVRIYLCR

51 EMAGSGTCGT VVSTTNFIKA EYKGRVTLKQ YPRKNLFLVE VTQLTESDSG

101 VYACGAGMNT DRGKTQKVTL NVHSEYEPSW EEQPMPETPK WFHLPYLFQM

151 PAYASSSKFV TRVTTPAQRG KVPPVHHSSP TTQITHRPRV SRASSVAGDK

201 PRTFLPSTTA SKISALEGLL KPQTPSYNHH TRLHRQRALD YGSQSGREGQ

251 GFHILIPTIL GLFLLALLGL VVKRAVERRK ALSRRARRLA VRMRALESSQ

301 RPRGSPRPRS QNNIYSACPR RARGADAAGT GEAPVPGPGA PLPPAPLQVS

351 ESPWLHAPSL KTSCEYVSLY HQPAAMMEDS DSDDYINVPA
```

ᵇAn amino acid sequence of a human PIGRL-1 (SEQ ID NO: 2).

One polynucleotide of the present invention encoding PIGRL-1 may be obtained using standard cloning and screening, from a cDNA library derived from mRNA in cells of human fetal heart, tonsils, bone marrow and leukocytes using the expressed sequence tag (EST) analysis (Adams, M. D., et al. *Science* (1991) 252:1651–1656; Adams, M. D. et al., *Nature*, (1992) 355:632–634; Adams, M. D., et al, *Nature* (1995) 377 Supp:3–174). Polynucleotides of the invention can also be obtained from natural sources such as genomic DNA libraries or can be synthesized using well known and commercially available techniques.

The nucleotide sequence encoding PIGRL-1 polypeptide of SEQ ID NO:2 may be identical to the polypeptide encoding sequence contained in Table 1 (nucleotide number 146 to 1315 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of PIGRL-1 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain noncoding 5' and 3' sequences, such as transcribed, non-translated sequences, splicing and polyadenylation signals, ribosome binding sites and sequences that stabilize mRNA.

Further preferred embodiments are polynucleotides encoding PIGRL-1 variants comprising the amino acid sequence PIGRL-1 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3ᶜ

```
  1 GGCAGAGCCT CATGGTCACG AGCTTTGTTC CTCGTGGGGG CTAGAAATCT

51 CTTTCCAGTT CCAGATTGTG AAGGGTTCCT GAGTAAGCAG CGTGTCTCCA

101 TCCCCCTCTC TAGGGGCTCT TGGATGGACC TTGCACTCTA GAAGGGACAA

151 TGGACTTCTG GCTTTGGCCA CTTTACTTCC TGCCAGTATC AGGGGCCCTG

201 AGGATCCTCC CAGAAGTAAA GGTAGAGGGG GAGCTGGGCG GATCAGTTAC

251 CATCAAGTGC CCACTTCCTG AAATGCATGT GAGGATATAT CTGTGCCGGG

301 AGATGGCTGG ATCTGGAACA TGTGGTACCG TGGTATCCAC CACCAACTTC

351 ATCAAGGCAG AATACAAGGG CCGAGTTACT CTGAAGCAAT ACCCACGCAA
```

TABLE 3ᶜ-continued

```
 401 GAATCTGTTC CTAGTGGAGG TAACACAGCT GACAGAAAGT GACAGCGGAG

451 TCTATGCCTG CGGACGGGCA TGAACACAGA CCGGGGAAAG ACCCAGAAAG

501 TCACCCTGAA TGTCCACAGT GAATACGAGC CATCATGGGA AGAGCAGCCA

551 ATGCCTGAGA CTCCAAAATG GTTTCATCTG CCCTATTTGT TCCAGATGCC

601 TGCATATGCC GGTTCTTCCA CATTCGTAAC CGCAGAGTTA CCACACCAGC

651 TTCAAAGGGG CAAGGTCCCT CCAGTTCACC ACTCCTCCCC CACCACCCAA

701 ATTCACCCAC CGCCCTTCGA GTGTNCAGAG CATCTTCAGT AGCAGGTGAC

751 AAGCCCCGAA ACTTTCCTGC CATCCACTAC AGCCTCAAAA ATCTCAGCTC

801 TGGAAGGGCT GCTTCAAGCC CCAGAAGCGC CCAGCTACAA CANCACACCA

851 GGCTGCACAG GCAGAGAGCA CTGGATACTT ATGGGNTCAC AGTCTGGGGA

901 GGGGAANGNC CAAGGATTTT NACATTCCTG ATTCCCGGAC CATCNTTGGG

951 GCCTTTTTNC CTGGCTGGGG CAATTTCTGG GGGCTGGGTG GTTGAAAAAG

1001 GGGCCCNTTG GAAAAGGGAG GGAAAAGGNC TTTTTNCCAN GGCGGGG
```

ᶜA partial nucleotide sequence of a human PIGRL-1 (SEQ ID NO: 3).

TABLE 4ᵈ

```
  1 MDFWLWPLYF LPVSGALRIL PEVKVEGELG GSVTIKCPLP EMVVRIYLCR

51 EMAGSGTCGT WSTTNFIKA EYKGRVTLKQ YPRKNLFLVE VTQLTESDSG

101 VYACGRA
```

ᵈA partial amino acid sequence of a human PIGRL-1 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment thereof, may be used as hybridization probes for cDNA and genomic DNA, to isolate full-length cDNAs and genomic clones encoding PIGRL-1 and to isolate cDNA and genomic clones of other genes (including genes encoding homologs and orthologs from species other than human) that have a high sequence similarity to the PIGRL-1 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding PIGRL-1 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Stringent hybridization conditions are as defined above or alternatively conditions under overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the PIGRL-1 polypeptide is to be expressed for use in screening assays, generally, it is preferred that the polypeptide be produced at the surface of the cell. In this event, the cells may be harvested prior to use in the screening assay. If PIGRL-1 polypeptide is secreted into the medium, the medium can be recovered in order to recover and purify the polypeptide; if produced intracellularly, the cells must first be lysed before the polypeptide is recovered.

PIGRL-1 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of PIGRL-1 polynucleotides for use as diagnostic reagents. Detection of a mutated form of PIGRL-1 gene associated with a dysfunction will provide a diagnostic tool that can add to or define a diagnosis of a disease or susceptibility to a disease which results from under-expression, over-expression or altered expression of PIGRL-1. Individuals carrying mutations in the PIGRL-1 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PIGRL-1 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., Science (1985) 230:1242. Sequence changes at specific locations may also be revealed by nuclease protection assays, such as RNase and S1 protection or the chemical cleavage method. See Cotton et al., Proc Natl Acad Sci USA (1985) 85: 4397–4401. In another embodiment, an array of oligonucleotides probes comprising PIGRL-1 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M.Chee et al., Science, Vol 274, pp 610–613 (1996)).

The diagnostic assays offer a process for diagnosing or determining a susceptibility to Hyper-IgM Immunodeficiency (HIM), X-linked Severe Combined Immunodeficiency (XSCID), and IgA deficiency (IgA-D) through detection of mutation in the PIGRL-1 gene by the methods described.

In addition, Hyper-IgM Innunodeficiency (HIM), X-linked Severe Combined Immunodeficiency (XSCID), and IgA deficiency (IgA-D), can be diagnosed by methods comprising determining from a sample derived from a subject an abnormally decreased or increased level of PIGRL-1 polypeptide or PIGRL-1 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an PIGRL-1, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly Hyper-IgM Immunodeficiency (HIM), X-inked Severe Combined Immunodeficiency (XSCID), and IgA deficiency (IgA-D), which comprises:

(a) a PIGRL-1 polynucleotide, preferably the nucleotide sequence of SEQ ID NO: 1, or a fragment thereof;

(b) a nucleotide sequence complementary to that of (a);

(c) a PIGRL-1 polypeptide, preferably the polypeptide of SEQ ID NO: 2, or a fragment thereof, or (d) an antibody to a PIGRL-1 polypeptide, preferably to the polypeptide of SEQ ID NO: 2.

It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the PIGRL-1 polypeptides. The term "immunospecific" means that the antibodies have substantial greater affinity for the polypeptides of the invention than their affinity for other related polypeptides in the prior art.

Antibodies generated against the PIGRL-1 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against PIGRL-1 polypeptides may also be employed to treat Hyper-IgM Immunodeficiency (HIM), X-linked Severe Combined Immunodeficiency (XSCID), and IgA deficiency (IgA-D), among others.

Vaccines

Another aspect of the invention relates to a method for inducing an immunological response in a mammal which comprises inoculating the mammal with PIGRL-1 polypeptide, or a fragment thereof, adequate to produce antibody and/or T cell immune response to protect said animal from Hyper-IgM Immunodeficiency (HIM), X-linked Severe Combined Immunodeficiency (XSCID), and IgA deficiency (IgA-D), among others. Yet another aspect of the invention relates to a method of inducing immunological response in a mammal which comprises, delivering PIGRL-1 polypeptide via a vector directing expression of PIGRL-1 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a PIGRL-1 polypeptide wherein the composition comprises a PIGRL-1 polypeptide or PIGRL-1 gene. The vaccine formulation may further comprise a suitable carrier. Since PIGRL-1 polypeptide may be broken down in the stomach, it is preferably administered parenterally (including subcutaneous, intramuscular, intravenous, intradermnal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The PIGRL-1 polypeptide of the present invention may be employed in a screening process for compounds which bind the receptor and which activate (agonists) or inhibit activation of (antagonists) the receptor polypeptide of the present invention. Thus, polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunoloagy* 1(2):Chapter 5 (1991).

PIGRL-1 polypeptides are responsible for many biological functions, including many pathologies. Accordingly, it is desirous to find compounds and drugs which stimulate PIGRL-1 on the one hand and which can inhibit the function of PIGRL-1 on the other hand. In general, agonists are employed for therapeutic and prophylactic purposes for such conditions as Hyper-IgM Immunodeficiency (HIM), X-linked Severe Combined Immunodeficiency (XSCID), and IgA deficiency (IgA-D). Antagonists may be employed for a variety of therapeutic and prophylactic purposes for such conditions as Hyper-IgM Immunodeficiency (HIM), X-inked Severe Combined Immunodeficiency (XSCID), and IgA deficiency (UgA-D).

In general, such screening procedures involve producing appropriate cells which express the receptor polypeptide of the present invention on the surface thereof Such cells include cells from mammals, yeast, Drosophila or E. coli. Cells expressing the receptor (or cell membrane containing the expressed receptor) are then contacted with a test compound to observe binding, or stimulation or inhibition of a functional response.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a PIGRL-1 polypeptide to form a mixture, measuring PIGRL-1 activity in the mixture, and comparing the PIGRL-1 activity of the mixture to a standard.

The PIGRL-1 cDNA, protein and antibodies to the protein may also be used to configure assays for detecting the effect of added compounds on the production of PIGRL-1 mRNA and protein in cells. For example, an ELISA may be constructed for measuring secreted or cell associated levels of PIGRL-1 protein using monoclonal and polyclonal antibodies by standard methods known in the art, and this can be used to discover agents which may inhibit or enhance the production of PIGRL-1 (also called antagonist or agonist, respectively) from suitably manipulated cells or tissues. Standard methods for conducting screening assays are well understood in the art.

Examples of potential PIGRL-1 antagonists include antibodies or, in some cases, oligonucleotides or proteins which are closely related to the ligand of the PIGRL-1, e.g., a fragment of the ligand, or small molecules which bind to the receptor but do not elicit a response, so that the activity of the receptor is prevented.

Thus in another aspect, the present invention relates to a screening kit for identifying agonists, antagonists, ligands, receptors, substrates, enzymes, etc. for PIGRL-1 polypeptides; or compounds which decrease or enhance the production of PIGRL-1 polypeptides, which comprises:

(a) a PIGRL-1 polypeptide, preferably that of SEQ ID NO:2;

(b) a recombinant cell expressing a PIGRL-1 polypeptide, preferably that of SEQ ID NO:2;

(c) a cell membrane expressing a PIGRL-1 polypeptide; preferably that of SEQ ID NO: 2; or (d) antibody to a PIGRL-1 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating an abnormal conditions related to both an excess of and insufficient amounts of PIGRL-1 activity.

If the activity of PIGRL-1 is in excess, several approaches are available. One approach comprises administering to a subject an inhibitor compound (antagonist) as hereinabove described along with a pharmaceutically acceptable carrier in an amount effective to inhibit activation by blocking binding of ligands to the PIGRL-1, or by inhibiting a second signal, and thereby alleviating the abnormal condition.

In another approach, soluble forms of PIGRL-1 polypeptides still capable of binding the ligand in competition with endogenous PIGRL-1 may be administered. Typical embodiments of such competitors comprise fragments of the PIGRL-1 polypeptide.

In still another approach, expression of the gene encoding endogenous PIGRL-1 can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an underexpression of PIGRL-1 and its activity, several approaches are also available. One approach comprises administering to a subject a therapeutically effective amount of a compound which activates PIGRL-1, i.e., an agonist as described above, in combination with a pharmaceutically acceptable carrier, to thereby alleviate the abnormal condition. Alternatively, gene therapy may be employed to effect the endogenous production of PIGRL-1 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of PIGRL-1 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of admnistration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

While there are several methods to obtain the full length cDNA, two are outlined below. 1) The method of Rapid Amplification of cDNA Ends (RACE) can be utilized to obtain the 5' end. See Frohman et al., Proc. Nat. Acad. Sci USA 85, 8998–9002. (1988). Briefly, specific oliognucleotides are annealed to mRNA and used to prime the synthesis of the cDNA strand. Following destruction of the mRNA with RNaseH, a poly C anchor sequence is added to the 3' end of the cDNA and the resulting fragment is amplified using a nested set of antisense primers and an anchor sequence primer. The amplified fragment is cloned into an appropriate vector and subjected to restriction and sequence analysis.

2) The polymerase chain reaction can be used to amplify the 5' end of the cDNA from human cDNA libraries using sequential rounds of nested PCR with two sets of primers. One set of antisense primers is specific to the 5' end of the partial cDNA and the other set of primers anneals to a vector specific sequence. The amplified products are cloned into an appropriate vector and subjected to restriction and sequence analysis.

Example 2.

PIGRL-1 Belongs to Immunoglobulin (Ig) Superfamily.

PIGRL-1 is a new member of the Ig family. The predicted partial protein sequence of this new gene shows modest, but extended, homology to polymeric Ig receptor (pIgR). The pIgR plays a crucial role in mucosal immunity by translocating polymeric IgA and IgM through secretory epithelial cells into external body fluids (J. P. Kraehenbuhl et al., Physiol. Rev. 72:853–879, 1992), an important process in defense against the invasion of microbial pathogens. Based on the multiple tissue dot blot and northern blot data, Expression of PIGRL-1 is restricted to the immune system, suggesting a role in immune function and a candidate for drug targeting.

The extracellular region of PIGRL-1 contains a single Ig domain with a V-like fold as shown by (1) the presence of Ig V fold conserved residues and (2) homology to several other Ig like proteins (poly Ig V1 and V4, CMRF35, TCR Vβ and Ig κ $V_L$).

In the following alignment, dashes indicate positions where residues are identical to the V1 region of the poly Ig receptor (poly Ig RV1). Residues in poly Ig RV1 that are highly conserved in Ig variable regions (A. N. Barclay et al., The leukocyte antigen facts book, 2nd edition, Academic Press, 1997) are shown in bold.

|  |  | B |  |  | C | C' |  |
|---|---|---|---|---|---|---|---|
| PIGRL-1 | --pevk-ege | 1-g--t-k-p | 1-....em-v | -i-1-.-ema | -g-st...-g- | | 42 (SEQ ID NO: 4) |
| CMRF3S | lsh-mt-agp | v-g-1--q-r | -eke...h-tl | n-----.r-p | qilr...-dk | | 43 (SEQ ID NO: 5) |
| PolyIgRV4 | prs-tv-kg- | a-s--a-1-p | -nrk...esks | i----1-ega | qn-r...-pl | | 45 (SEQ ID NO: 6) |
| Ig κ $V_L$ | tqt-as-eva | v-gt-t-k-q | asqsis...- | yls--qqk-- | q-pk-li-.. | | 45 (SEQ ID NO: 7) |
| TCR Vβ | sqk-srdicq | r-t-lt-q-q | v.dsq-...- | mm---rq--- | qslt-iatan | | 46 (SEQ ID NO: 8) |
| PolyIgRV1 | ---------- | ---------- | ---------- | -----.--.- | ----...--- | | |
| Consensus | IFGPEEVNSV C" | EGNSVSITCY D | YPPTSVNRHT E | RKYWC-RQPG | ARGGL--CIT F | | 47 (SEQ ID NO: 9) |
| PIGRL-1 | v--ttn--ka | e-k--vt-kq | --rknl-1-e | -t--tes--- | v-a--a-m-t | | 92 (SEQ ID NO: 4) |
| CMRF3S | i-etk-sa.g | -rn--vsird | s-a-ls-t-t | len-te--a- | t-w--vdtpw | | 92 (SEQ ID NO: 5) |
| PolyIgRV4 | --d-----ka | q-e--ls-le | e-g----t-i | ln--tsr-a- | f-w-ltngdt | | 95 (SEQ ID NO: 6) |
| Ig κ $V_L$ | ..rast-a-g | .vss-fkgsg | .sgtef.tlt | -sgveca-aa | t-y-qq-ws- | | 92 (SEQ ID NO: 7) |
| TCR Vβ | qg-eat-e-g | fvidkfpisr | .-nltfstlt | -sn--p---s | i-1-sve.ge | | 94 (SEQ ID NO: 8) |
| PolyIgRV1 | ---------- | ---------- | ---------- | ---------- | --------- | | |
| Consensus | LISSEGYVSS | KYAGRANLTN | FPENGTFVVN | IAQLSQDDSG | RYKCGLGINS | | 97 (SEQ ID NO: 9) |
| PIGRL-1 | d--ktqk-t- | n- | (SEQ ID NO: 4) | | | | |
| CMRF35 | --d-.h-piv | -- | (SEQ ID NO: 5) | | | | |
| PolyIgRV4 | --....rttv | -- | (SEQ ID NO: 6) | | | | |
| Ig κ $V_L$ | snvenvfg.. | .. | (SEQ ID NO: 7) | | | | |

| | | | |
|---|---|---|---|
| TCR Vβ | agdtq-fgp. | .. | (SEQ ID NO: 8) |
| PolyIgRV1 | .--------- | - | |
| Consensus | LRGLSFDVSL | EV | (SEQ ID NO: 9) |

Example 3.

PIGRL-1 Gene Expression Pattern:

PIGRL-1, a new member of the Ig superfamily, has been identified. The predicted protein sequence of this new gene shows modest, but extended, homology to polymeric Ig receptor family proteins, particularly in the extracellular domain. Based on the Clontech's Human RNA Master Blot and Multiple Tissue Northern Blot results, PIGRL-1 is exclusively expressed in spleen, thymus, lymph nodes and peripheral leukocytes, suggesting a role in immune function. Thus, this protein is a candidate target for diseases of the immune system such as Hyper-IgM Immunodeficiency, X-linked Severe Combined Immunodeficiency (XSCID), and IgA deficiency (IgA-D)

Example 4.

Recombinant Soluble PIGRL-1 Proteins.

The extracellular domain of PIGRL-1 is expressed as a secreted soluble protein by truncation at the start of the transmembrane domain (glycine 251 in Table 2) as has been described for other immunoglobulin domain proteins, e.g. for CD4 (K. C. Deen et al., Nature 331: 82–84 (1988)). PIGRL-1 is also expressed as a secreted, soluble Ig fusion protein by linking the same extracellular region of PIGRL-1 to the hinge and constant domains of heavy chain IgG such as has been described for CD4 (D. J. Capon et al., Nature 317: 525–531 (1989)). In addition, preparation of oligomeric Ig fusion proteins is possible by addition of the tailpiece segment of IgM or IgA to the C-terminus of the Fc domain of IgGs, as exemplified for the IgM tailpiece segment in R. I. F. Smith and S. L. Morrison, Biotechnology 12: 683–688 (1994) and in R. I. F. Smith, et al., J. Immunol. 154: 2226–2236 (1995). These proteins are produced in insect cells or in mammalian cells such as COS-7 or CHO, purified by standard methodology, and are useful as tool, therapeutic, and diagnostic agents. Thus, these proteins are used to:

a) Determine the cleavage site of the N-terminal leader by amino acid sequence analysis of this processed recombinant protein.

b) Prepare polyclonal and monoclonal antibodies for:
   1) Detection of PIGRL-1 protein expression in different tissues and cell types.
   2) Functional studies of PIGRL-1 protein, such as induction of cell differentiation and proliferation, cytokine production, and cell death assays.

c) Test for agonist/antagonist activity when added to cultured cells and in animal models of immune disease.

d) Search for its ligand(s).

e) Establish screen assays for small molecule agonists or antagonists of PIGRL-1 protein, which may be potential therapeutic and/or diagnostic agents.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide comprising a nucleotide sequence that encodes the amino acid sequence set forth in SEQ ID NO:2; or a nucleotide sequence fully complementary to said isolated polynucleotide.

2. The isolated polynucleotide of claim 1 wherein said polynucleotide comprises the nucleotide sequence contained in SEQ ID NO:1 encoding the PIGRL-1 polypeptide of SEQ ID NO:2.

3. The isolated polynucleotide of claim 1 wherein said polynucleotide comprises the nucleotide sequence set forth in SEQ ID NO: 1.

4. The isolated polynucleotide of claim 3 consisting of the nucleotide sequence set forth in SEQ ID NO:1.

5. The isolated polynucleotide of claim 1 which is DNA or RNA.

6. An expression system comprising an isolated polynucleotide, wherein said expression system produces a polypeptide comprising the amino acid sequence set forth in SEQ ID NO:2 when said expression system is present in a compatible host cell.

7. An isolated host cell comprising the expression system of claim 6.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 2040 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ACGAGCCTCA TCGTCAAGCT TTGTTCCTCG TGGGGGCTAG AAATCTCTTT CCAGTTCCAG      60

ATTGTGAAGG GTTCCTGAGT AAGCAGCGTG TCTCCATCCC CCTCTCTAGG GGCTCTTGGA     120

TGGACCTTGC ACTCTAGAAG GGACAATGGA CTTCTGGCTT TGGCCACTTT ACTTCCTGCC     180

AGTATCAGGG GCCCTGAGGA TCCTCCCAGA AGTAAAGGTA GAGGGGAGC TGGGCGGATC      240

AGTTACCATC AAGTGCCCAC TTCCTGAAAT GCATGTGAGG ATATATCTGT GCCGGGAGAT     300

GGCTGGATCT GGAACATGTG GTACCGTGGT ATCCACCACC AACTTCATCA AGGCAGAATA     360
```

-continued

```
CAAGGGCCGA GTTACTCTGA AGCAATACCC ACGCAAGAAT CTGTTCCTAG TGGAGGTAAC      420

ACAGCTGACA GAAAGTGACA GCGGAGTCTA TGCCTGCGGA GCGGGCATGA ACACAGACCG      480

GGGAAAGACC CAGAAAGTCA CCCTGAATGT CCACAGTGAA TACGAGCCAT CATGGGAAGA      540

GCAGCCAATG CCTGAGACTC CAAAATGGTT TCATCTGCCC TATTTGTTCC AGATGCCTGC      600

ATATGCCAGT TCTTCCAAAT TCGTAACCAG AGTTACCACA CCAGCTCAAA GGGGCAAGGT      660

CCCTCCAGTT CACCACTCCT CCCCCACCAC CCAAATCACC CACCGCCCTC GAGTGTCCAG      720

AGCATCTTCA GTAGCAGGTG ACAAGCCCCG AACCTTCCTG CCATCCACTA CAGCCTCAAA      780

AATCTCAGCT CTGGAGGGGC TGCTCAAGCC CCAGACGCCC AGCTACAACC ACCACACCAG      840

GCTGCACAGG CAGAGAGCAC TGGACTATGG CTCACAGTCT GGGAGGGAAG GCCAAGGATT      900

TCACATCCTG ATCCCGACCA TCCTGGGCCT TTTCCTGCTG GCACTTCTGG GGCTGGTGGT      960

GAAAAGGGCC GTTGAAAGGA GGAAAGCCCT CTCCAGGCGG GCCCGCCGAC TGGCCGTGAG     1020

GATGCGCGCC CTGGAGAGCT CCCAGAGGCC CCGCGGGTCG CCGCGACCGC GCTCCCAAAA     1080

CAACATCTAC AGCGCCTGCC CGCGGCGCGC TCGTGGAGCG GACGCTGCAG GCACAGGGGA     1140

GGCCCCCGTT CCCGGCCCCG GAGCGCCGTT GCCCCCCGCC CCGCTGCAGG TGTCTGAATC     1200

TCCCTGGCTC CATGCCCCAT CTCTGAAGAC CAGCTGTGAA TACGTGAGCC TCTACCACCA     1260

GCCTGCCGCC ATGATGGAGG ACAGTGATTC AGATGACTAC ATCAATGTTC CTGCCTGACA     1320

ACTCCCCAGC TATCCCCCAA CCCCAGGCTC GGACTGTGGT GCCAAGGAGT CTCATCTATC     1380

TGCTGATGTC CAATACCTGC TTCATGTGTT CTCAGAGCCC TCATCACTTC CCATGCCCCA     1440

TCTCGACTCC CATCCCCATC TATCTGTGCC CTGAGCATGG CTCTGCCCCC AGGTCGTCTT     1500

GCACACCTTG GCAGCCCCCT GTAGTTGACA GGTAAGCTGT AGGCATGTAG AGCAATTGTC     1560

CCAATGCCAC TTGCTTCCTT TCCAAGCCGT CGAACAGACT GTGGGATTTG CAGAGTGTTT     1620

CTTCCATGTC TTTGACCACA GGGTTGTTGC TGCCCAGGCT CTAGATCACA TGGCATCAGG     1680

CTGGGGCAGA GGCATAGCTA TTGTCTCGGG CATCCCTTCC CAGGGTTGGG TCTTACACAA     1740

ATAGAAGGCT CTTGCTCTGA GTTATGTGAC ATGCCTCAGC CCCATGGACT AAGCAGGGGT     1800

CTGGTATAAA AACACTCCTG GAAACGCCTT TGCCCTGATC CAAATGTTAG CACTTGCTAG     1860

TGAACGTCTA CTTATCTCAA GTTCTATGCT AAAGGCAATT TATCTTGATG TGATGATAAA     1920

CCAAACTTAT TAGCAAGATA TGCATATATA TCCATAAATT CTCTTTACTC TGTCTCCATC     1980

ACTTGATGCA CATAAGTGCC CTGACCTCAG CATCTCCCCT CTAAAAAAAA AAAAAAAAA      2040
```

(2) INFORMATION FOR SEQ ID NO:2:

(i) SEQUENCE CHARACTERISTICS:
        (A) LENGTH: 390 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Asp Phe Trp Leu Trp Pro Leu Tyr Phe Leu Pro Val Ser Gly Ala
 1               5                  10                  15

Leu Arg Ile Leu Pro Glu Val Lys Val Glu Gly Leu Gly Gly Ser
            20                  25                  30

Val Thr Ile Lys Cys Pro Leu Pro Glu Met His Val Arg Ile Tyr Leu
        35                  40                  45

Cys Arg Glu Met Ala Gly Ser Gly Thr Cys Gly Thr Val Val Ser Thr
```

```
        50                  55                  60
Thr Asn Phe Ile Lys Ala Glu Tyr Lys Gly Arg Val Thr Leu Lys Gln
 65                  70                  75                  80

Tyr Pro Arg Lys Asn Leu Phe Leu Val Glu Val Thr Gln Leu Thr Glu
                 85                  90                  95

Ser Asp Ser Gly Val Tyr Ala Cys Gly Ala Gly Met Asn Thr Asp Arg
                100                 105                 110

Gly Lys Thr Gln Lys Val Thr Leu Asn Val His Ser Glu Tyr Glu Pro
            115                 120                 125

Ser Trp Glu Glu Gln Pro Met Pro Glu Thr Pro Lys Trp Phe His Leu
130                 135                 140

Pro Tyr Leu Phe Gln Met Pro Ala Tyr Ala Ser Ser Lys Phe Val
145                 150                 155                 160

Thr Arg Val Thr Thr Pro Ala Gln Arg Gly Lys Val Pro Pro Val His
                165                 170                 175

His Ser Ser Pro Thr Thr Gln Ile Thr His Arg Pro Arg Val Ser Arg
                180                 185                 190

Ala Ser Ser Val Ala Gly Asp Lys Pro Arg Thr Phe Leu Pro Ser Thr
            195                 200                 205

Thr Ala Ser Lys Ile Ser Ala Leu Glu Gly Leu Leu Lys Pro Gln Thr
210                 215                 220

Pro Ser Tyr Asn His His Thr Arg Leu His Arg Gln Arg Ala Leu Asp
225                 230                 235                 240

Tyr Gly Ser Gln Ser Gly Arg Glu Gly Gln Gly Phe His Ile Leu Ile
                245                 250                 255

Pro Thr Ile Leu Gly Leu Phe Leu Leu Ala Leu Leu Gly Leu Val Val
                260                 265                 270

Lys Arg Ala Val Glu Arg Arg Lys Ala Leu Ser Arg Arg Ala Arg Arg
            275                 280                 285

Leu Ala Val Arg Met Arg Ala Leu Glu Ser Ser Gln Arg Pro Arg Gly
290                 295                 300

Ser Pro Arg Pro Arg Ser Gln Asn Asn Ile Tyr Ser Ala Cys Pro Arg
305                 310                 315                 320

Arg Ala Arg Gly Ala Asp Ala Ala Gly Thr Gly Glu Ala Pro Val Pro
                325                 330                 335

Gly Pro Gly Ala Pro Leu Pro Pro Ala Pro Leu Gln Val Ser Glu Ser
            340                 345                 350

Pro Trp Leu His Ala Pro Ser Leu Lys Thr Ser Cys Glu Tyr Val Ser
            355                 360                 365

Leu Tyr His Gln Pro Ala Ala Met Met Glu Asp Ser Asp Ser Asp Asp
    370                 375                 380

Tyr Ile Asn Val Pro Ala
385                 390
```

(2) INFORMATION FOR SEQ ID NO:3:

(i) SEQUENCE CHARACTERISTICS:
        (A) LENGTH: 1047 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCAGAGCCT CATGGTCACG AGCTTTGTTC CTCGTGGGGG CTAGAAATCT CTTTCCAGTT      60
```

```
CCAGATTGTG AAGGGTTCCT GAGTAAGCAG CGTGTCTCCA TCCCCCTCTC TAGGGGCTCT    120

TGGATGGACC TTGCACTCTA GAAGGGACAA TGGACTTCTG GCTTTGGCCA CTTTACTTCC    180

TGCCAGTATC AGGGGCCCTG AGGATCCTCC CAGAAGTAAA GGTAGAGGGG GAGCTGGGCG    240

GATCAGTTAC CATCAAGTGC CCACTTCCTG AAATGCATGT GAGGATATAT CTGTGCCGGG    300

AGATGGCTGG ATCTGGAACA TGTGGTACCG TGGTATCCAC CACCAACTTC ATCAAGGCAG    360

AATACAAGGG CCGAGTTACT CTGAAGCAAT ACCCACGCAA GAATCTGTTC CTAGTGGAGG    420

TAACACAGCT GACAGAAAGT GACAGCGGAG TCTATGCCTG CGGACGGGCA TGAACACAGA    480

CCGGGGAAAG ACCCAGAAAG TCACCCTGAA TGTCCACAGT GAATACGAGC CATCATGGGA    540

AGAGCAGCCA ATGCCTGAGA CTCCAAAATG GTTTCATCTG CCCTATTTGT TCCAGATGCC    600

TGCATATGCC GGTTCTTCCA CATTCGTAAC CGCAGAGTTA CCACACCAGC TTCAAAGGGG    660

CAAGGTCCCT CCAGTTCACC ACTCCTCCCC CACCACCCAA ATTCACCCAC CGCCCTTCGA    720

GTGTNCAGAG CATCTTCAGT AGCAGGTGAC AAGCCCCGAA ACTTTCCTGC CATCCACTAC    780

AGCCTCAAAA ATCTCAGCTC TGGAAGGGCT GCTTCAAGCC CCAGAAGCGC CCAGCTACAA    840

CANCACACCA GGCTGCACAG GCAGAGAGCA CTGGATACTT ATGGGNTCAC AGTCTGGGGA    900

GGGGAANGNC CAAGGATTTT NACATTCCTG ATTCCCGGAC CATCNTTGGG GCCTTTTTNC    960

CTGGCTGGGG CAATTTCTGG GGGCTGGGTG GTTGAAAAAG GGGCCCNTTG GAAAAGGGAG   1020

GGAAAAGGNC TTTTTNCCAN GGCGGGG                                      1047

(2) INFORMATION FOR SEQ ID NO:4:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Met Asp Phe Trp Leu Trp Pro Leu Tyr Phe Leu Pro Val Ser Gly Ala
 1               5                  10                  15

Leu Arg Ile Leu Pro Glu Val Lys Val Glu Gly Glu Leu Gly Gly Ser
            20                  25                  30

Val Thr Ile Lys Cys Pro Leu Pro Glu Met His Val Arg Ile Tyr Leu
        35                  40                  45

Cys Arg Glu Met Ala Gly Ser Gly Thr Cys Gly Thr Val Val Ser Thr
    50                  55                  60

Thr Asn Phe Ile Lys Ala Glu Tyr Lys Gly Arg Val Thr Leu Lys Gln
65                  70                  75                  80

Tyr Pro Arg Lys Asn Leu Phe Leu Val Glu Val Thr Gln Leu Thr Glu
                85                  90                  95

Ser Asp Ser Gly Val Tyr Ala Cys Gly Arg Ala
            100                 105

(2) INFORMATION FOR SEQ ID NO:5:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:5:

```
Leu Ser His Met Thr Ala Gly Pro Val Gly Leu Gln Arg Glu Lys Glu
 1               5                  10                  15

His Thr Leu Asn Arg Pro Gln Ile Leu Arg Asp Lys Ile Glu Thr Lys
            20                  25                  30

Ser Ala Gly Arg Asn Val Ser Ile Arg Asp Ser Ala Leu Ser Thr Thr
            35                  40                  45

Leu Glu Asn Thr Glu Ala Thr Trp Val Asp Thr Pro Trp Asp His Pro
    50                  55                  60

Ile Val
65
```

(2) INFORMATION FOR SEQ ID NO:6:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Pro Arg Ser Thr Val Lys Gly Ala Ser Ala Leu Pro Asn Arg Lys Glu
 1               5                  10                  15

Ser Lys Ser Ile Leu Glu Gly Ala Gln Asn Arg Pro Leu Asp Lys Ala
            20                  25                  30

Gln Glu Leu Ser Leu Glu Glu Gly Thr Ile Asn Leu Thr Ser Arg Ala
            35                  40                  45

Phe Trp Leu Thr Asn Gly Asp Thr Arg Thr Thr Val
    50                  55                  60
```

(2) INFORMATION FOR SEQ ID NO:7:

(i) SEQUENCE CHARACTERISTICS:
        (A) LENGTH: 75 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Thr Gln Thr Ala Ser Glu Val Ala Val Gly Thr Thr Lys Gln Ala Ser
 1               5                  10                  15

Gln Ser Ile Ser Tyr Leu Ser Gln Gln Lys Gln Pro Lys Leu Ile Arg
            20                  25                  30

Ala Ser Thr Ala Gly Val Ser Ser Phe Lys Gly Ser Gly Ser Gly Thr
            35                  40                  45

Glu Phe Thr Leu Thr Ser Gly Val Glu Cys Ala Ala Ala Thr Tyr Gln
    50                  55                  60

Gln Trp Ser Ser Asn Val Glu Asn Val Phe Gly
65                  70                  75
```

(2) INFORMATION FOR SEQ ID NO:8:

(i) SEQUENCE CHARACTERISTICS:
        (A) LENGTH: 76 amino acids
        (B) TYPE: amino acid
        (C) STRANDEDNESS: single
        (D) TOPOLOGY: linear

```
        (ii) MOLECULE TYPE: protein (xi) SEQUENCE DESCRIPTION: SEQ ID NO:8:

Ser Gln Lys Ser Arg Asp Ile Cys Gln Arg Thr Leu Thr Gln Gln Val
1               5                   10                  15

Asp Ser Gln Met Met Arg Gln Gln Ser Leu Thr Ile Ala Thr Ala Asn
            20                  25                  30

Gly Gly Glu Ala Thr Glu Gly Phe Val Ile Asp Lys Phe Pro Ile Ser
        35                  40                  45

Arg Asn Leu Thr Phe Ser Thr Leu Thr Ser Asn Pro Ser Ile Leu Ser
    50                  55                  60

Val Glu Gly Glu Ala Gly Asp Thr Gln Phe Gly Pro
65                  70                  75

(2) INFORMATION FOR SEQ ID NO:9:

(i) SEQUENCE CHARACTERISTICS:
            (A) LENGTH: 109 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:9:

Ile Phe Gly Pro Glu Glu Val Asn Ser Val Glu Gly Asn Ser Val Ser
1               5                   10                  15

Ile Thr Cys Tyr Tyr Pro Pro Thr Ser Val Asn Arg His Thr Arg Lys
            20                  25                  30

Tyr Trp Cys Arg Gln Pro Gly Ala Arg Gly Gly Leu Cys Ile Thr Leu
        35                  40                  45

Ile Ser Ser Glu Gly Tyr Val Ser Ser Lys Tyr Ala Gly Arg Ala Asn
    50                  55                  60

Leu Thr Asn Phe Pro Glu Asn Gly Thr Phe Val Val Asn Ile Ala Gln
65                  70                  75                  80

Leu Ser Gln Asp Asp Ser Gly Arg Tyr Lys Cys Gly Leu Gly Ile Asn
            85                  90                  95

Ser Leu Arg Gly Leu Ser Phe Asp Val Ser Leu Glu Val
            100                 105
```